United States Patent [19]

Wells

[11] Patent Number: 5,237,175
[45] Date of Patent: Aug. 17, 1993

[54] REAGENT GAS CONTROL FOR AN ION TRAP MASS SPECTROMETER USED IN THE CHEMICAL IONIZATION MODE

[75] Inventor: Gregory J. Wells, Fairfield, Calif.

[73] Assignee: Varian Associates, Inc., Palo Alto, Calif.

[21] Appl. No.: 841,677

[22] Filed: Feb. 26, 1992

[51] Int. Cl.⁵ ............................................. H01J 49/04
[52] U.S. Cl. ..................... 250/288; 250/281; 250/282
[58] Field of Search ............ 250/288, 288 A, 289, 250/281, 282; 137/599.1; 141/65

[56] References Cited

U.S. PATENT DOCUMENTS

| | | | |
|---|---|---|---|
| 2,769,912 | 11/1956 | Lupfer et al. | 250/289 |
| 3,700,893 | 10/1972 | Seidenberg et al. | 250/289 |
| 3,943,363 | 3/1976 | Amblard | 250/288 |
| 3,968,675 | 7/1976 | Briggs | 250/288 |
| 3,997,298 | 12/1976 | McLafferty et al. | 250/288 |
| 4,495,414 | 1/1985 | Barrier et al. | 250/288 |

Primary Examiner—Paul M. Dzierzynski
Assistant Examiner—Kiet T. Nguyen

[57] ABSTRACT

A reagent gas flow control system for use with an ion trap mass spectrometer is shown. The gas reagent gas flows from a source through a first gas flow restrictor connected to the inputs of second and third gas flow restrictors. The output of the second restrictor is connected to the ion trap where reagent gas is used, and the output of the third restrictor is connected to a vacuum pump, which may be the roughing pump used by the ion trap. At least one of the three restrictors is a variable restrictor. The configuration of the present invention allows the use of simple and inexpensive parts to provide exacting flow control.

22 Claims, 4 Drawing Sheets

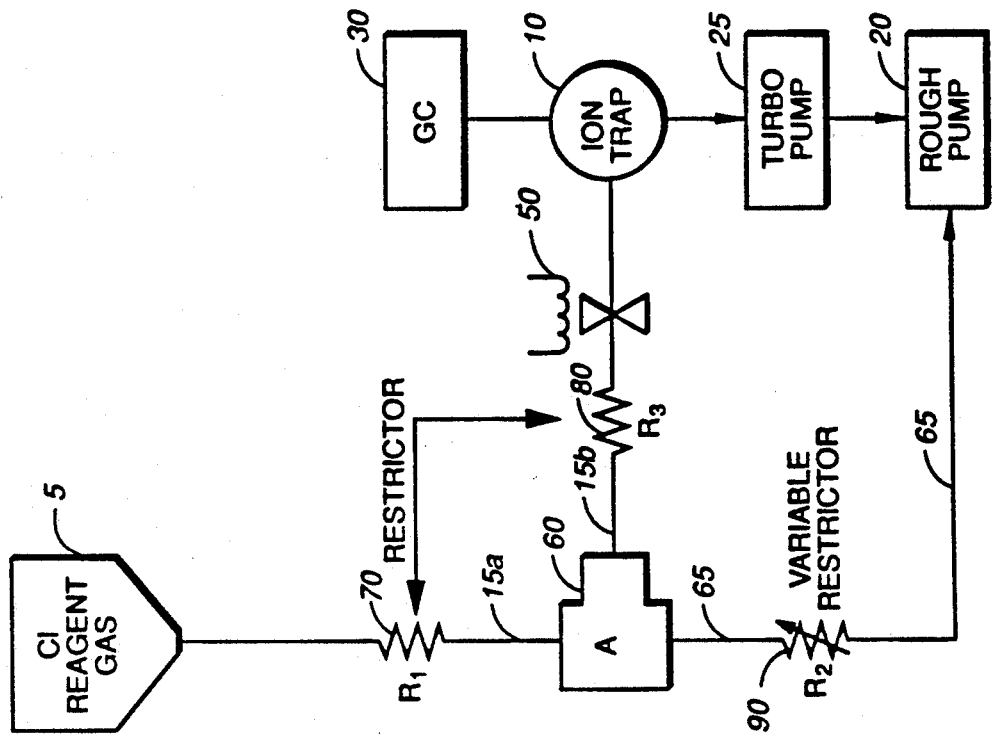
FIG._2
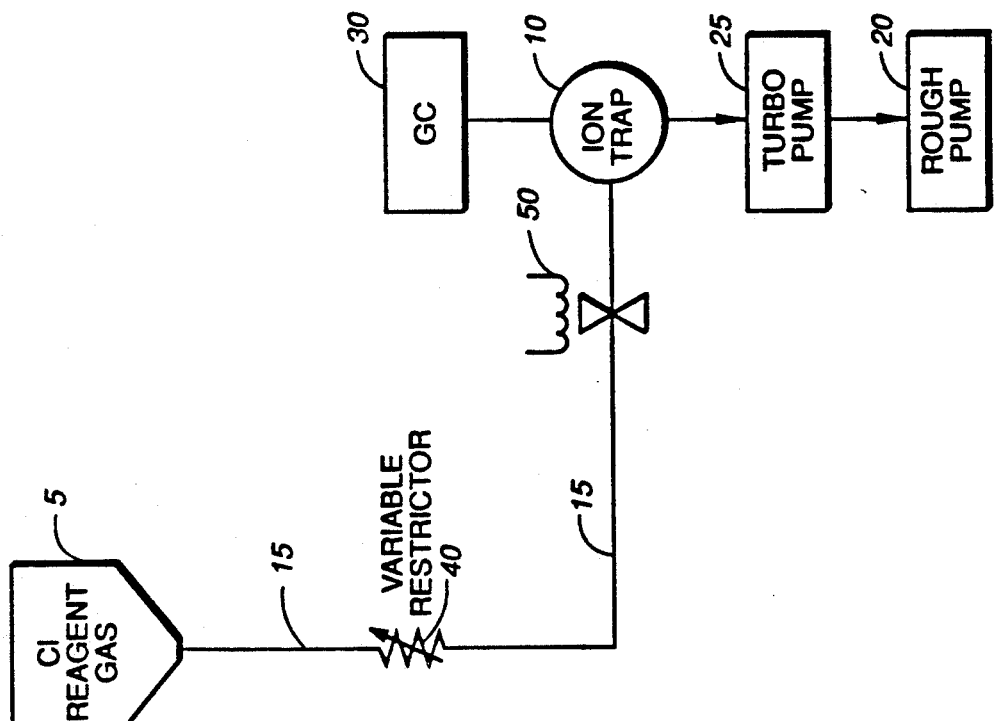
FIG._1
*(PRIOR ART)*

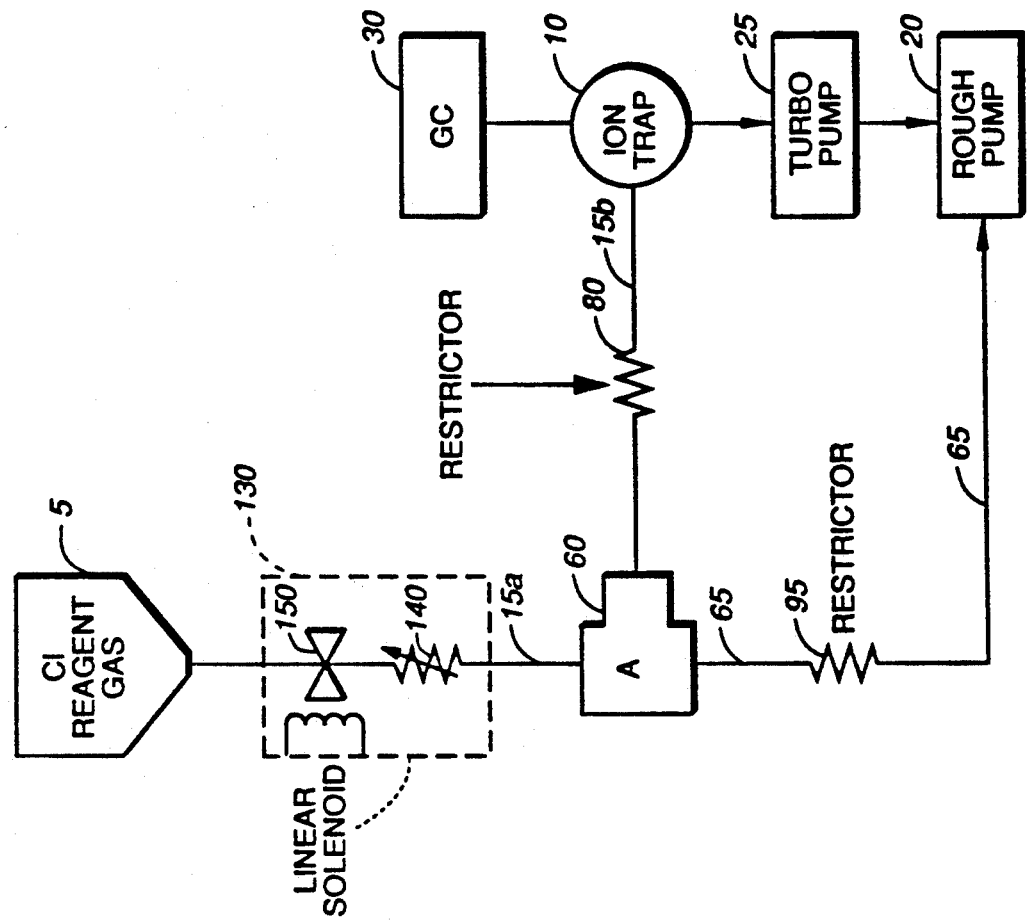
FIG._4
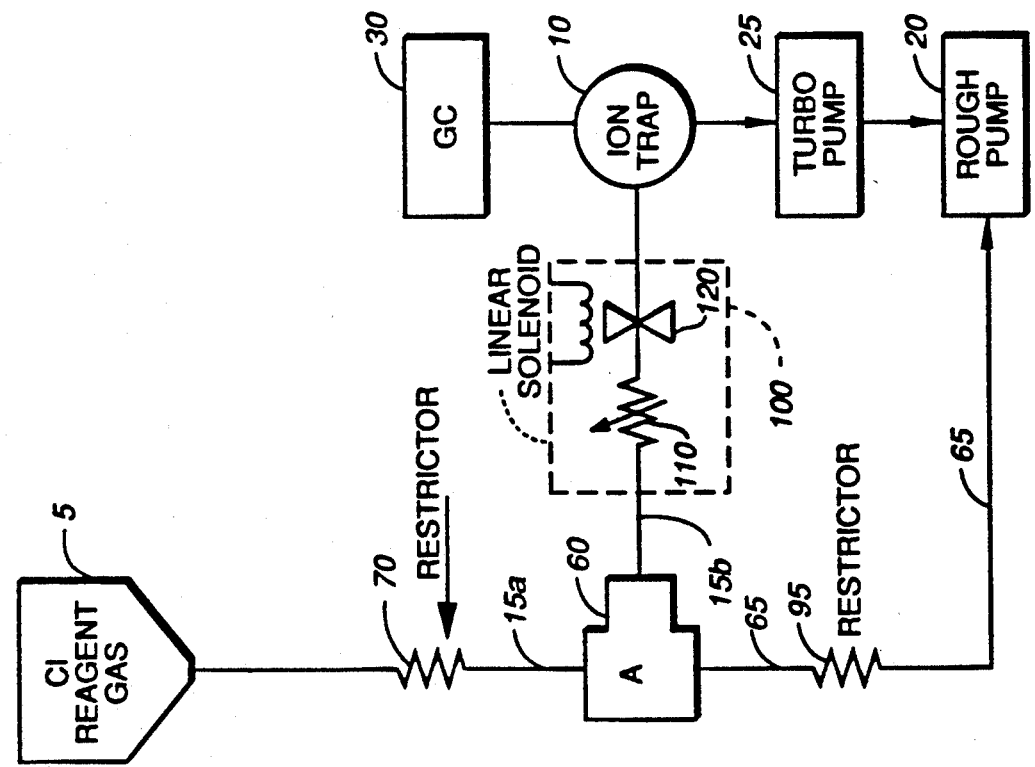
FIG._3

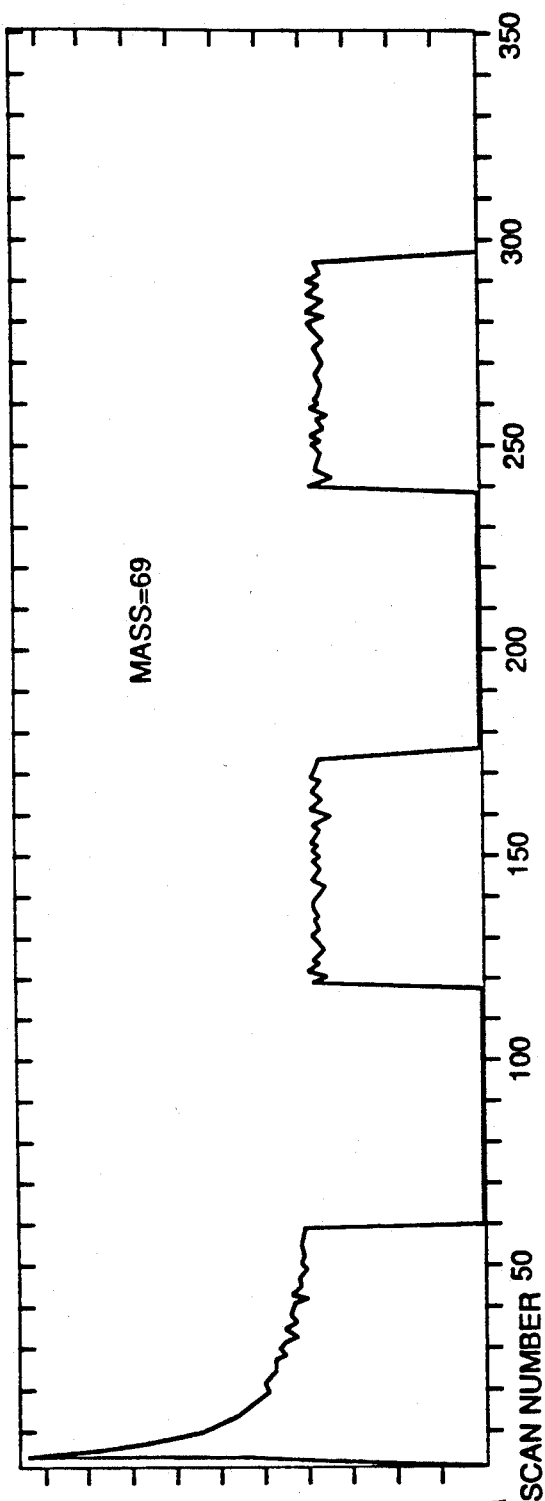
FIG._5A
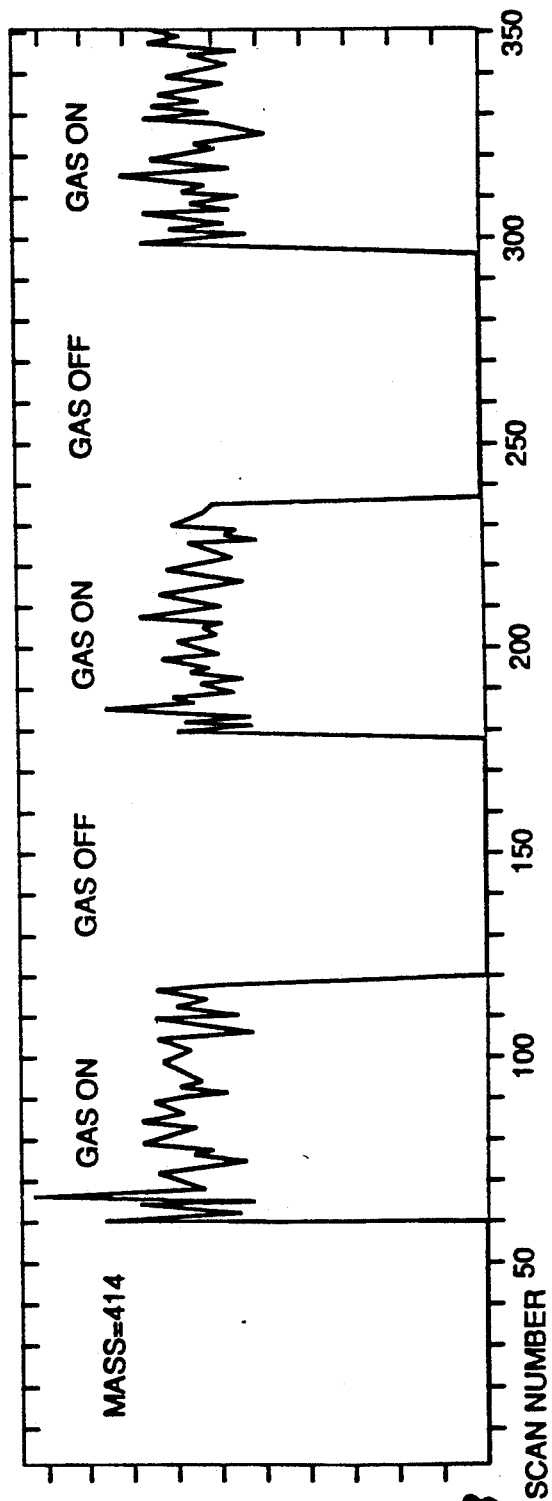
FIG._5B

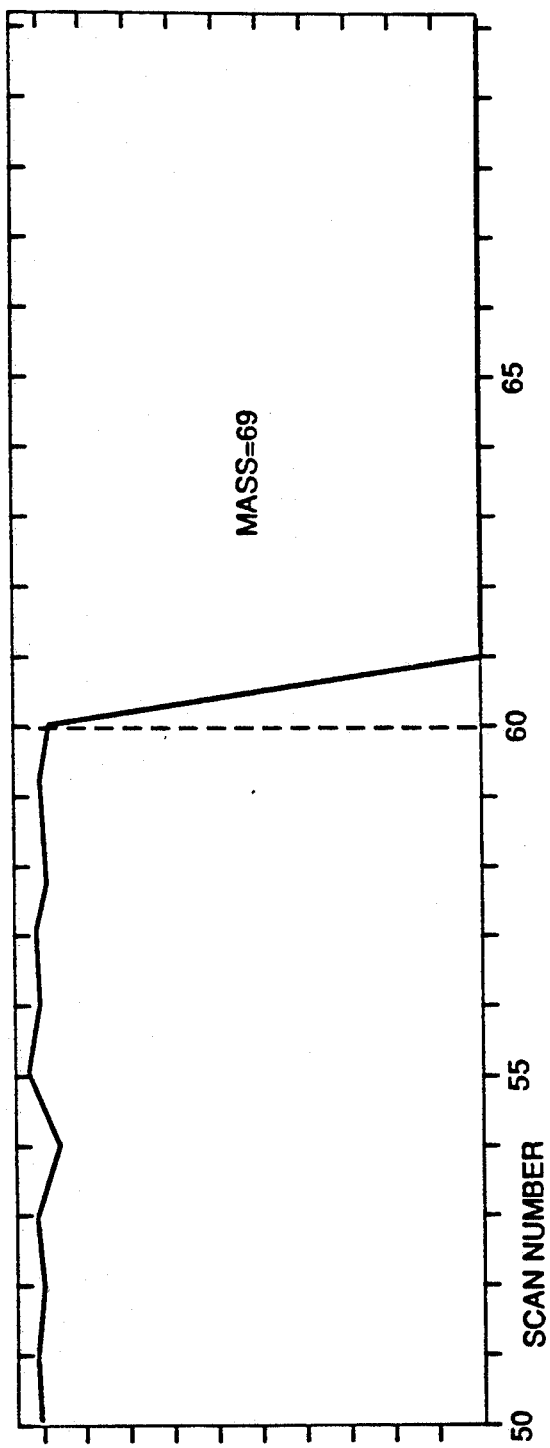
FIG._5C
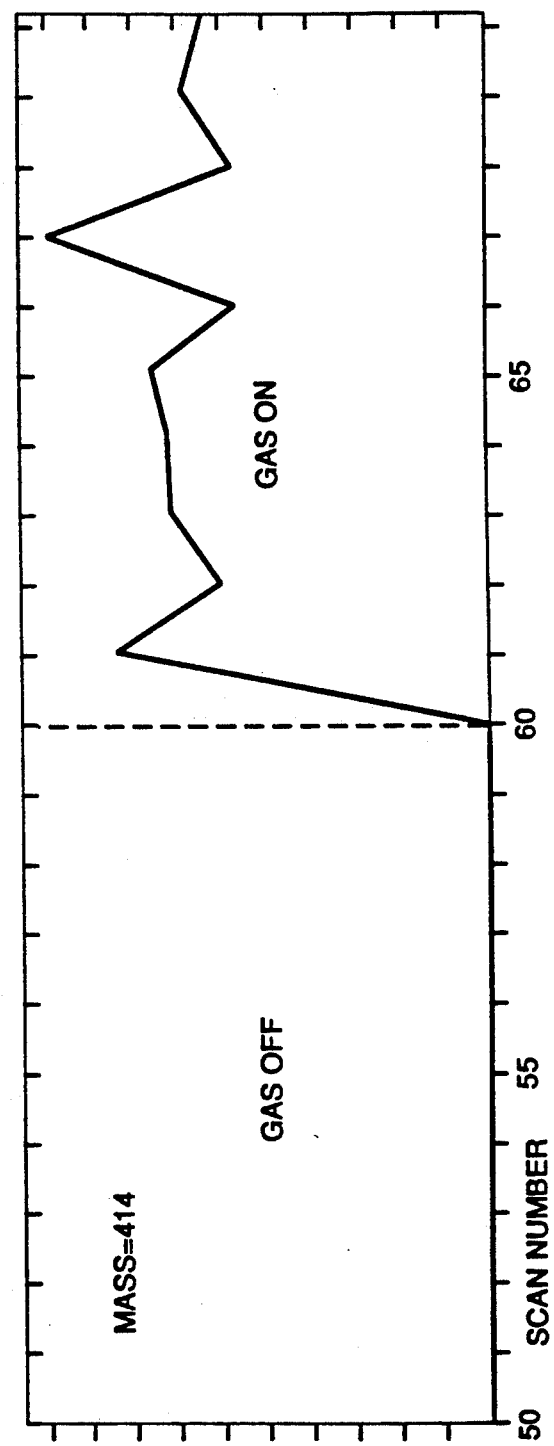
FIG._5D

REAGENT GAS CONTROL FOR AN ION TRAP MASS SPECTROMETER USED IN THE CHEMICAL IONIZATION MODE

FIELD OF THE INVENTION

The present invention relates to gas flow control systems and is particularly useful in connection with flow control of reagent gases used in ion trap mass spectrometers operating in the chemical ionization mode.

BACKGROUND OF THE INVENTION

The quadrupole ion trap, sometimes referred to as an ion store or an ion trap detector, is a well-known device for performing mass spectroscopy. A ion trap comprises a ring electrode and two coaxial end cap electrodes defining an inner volume. Each of the electrodes preferably has a hyperbolic surface, so that when appropriate AC and DC voltages are placed on the electrodes, a quadrupole trapping field is created. Typically, an ion trap is operated by introducing sample molecules into the ion trap where they are ionized. Depending on the operative trapping parameters, ions may be stably contained within the trap for relatively long periods of time. Under certain trapping conditions, a large range of masses may be simultaneously held within the trap. Various means are known for detecting ions that have been so trapped. One convenient method is to scan one or more of the trapping parameters so that ions become sequentially unstable and leave the trap where they may be detected using an electron multiplier. Another method is to use a resonance ejection technique whereby ions of consecutive masses can be scanned out of the trap and detected.

Several methods are known for ionizing sample molecules within the ion trap. Perhaps the most common method is to expose the sample to an electron beam. The impact of electrons with the sample molecules cause them to become ionized. This method is commonly referred to as electron impact ionization or "EI".

Another commonly used method of ionizing sample with an ion trap is chemical ionization or "CI". Chemical ionization involves the us of a reagent gas which is ionized, usually by EI within the trap, and allowed to react with sample molecules to form sample ions. Commonly used reagent gases include methane, isobutane, and ammonia. Chemical ionization is considered to be a "softer" ionization technique. With many samples CI produces fewer ion fragments than the EI technique, thereby simplifying mass analysis. Chemical ionization is a well known technique that is routinely used not only with quadrupole ion traps, but also with most other conventional types of mass spectrometers such as quadrupole mass filters, etc.

Most mass spectrometer systems used today include a gas chromatograph ("GC") as a sample separation and introduction device. When using a GC for this purpose, sample which elutes from the GC continuously flows into the mass spectrometer, which is set up to perform periodic mass analyses. Such analyses may, typically, be performed once a second. When performing CI experiments in such a system, a continuous flow of reagent gas is maintained.

Mass spectrometers operate at pressures that are greatly reduced below atmospheric pressure. A typical quadrupole ion trap operates at a pressure of $2 \times 10^{-2}$ Torr helium, and thus requires a continuous vacuum pumping system to maintain the desired vacuum level. When operating in the chemical ionization mode, reagent gas is introduced into the ion trap at 0.1 to 100 microTorr. This pressure range is far lower than the reagent gas pressure associated with other conventional mass spectrometers which typically operate using a reagent gas pressure of 0.5 to 50 Torr. One reason the reagent gas pressure is so much lower in an ion trap mass spectrometer is that the much longer residence time of the reagent ions in the trap allows for a much longer reaction period. In other conventional types of mass spectrometers, the reagent ions are present a much shorter time and, thus, much higher concentrations of reagent gas must be used to insure that sufficient numbers of sample ions are created by CI.

In a typical commercially available ion trap configuration, the vacuum enclosure is continuously pumped at a rate of 40 to 60 liters per second. To attain the desired partial pressure of reagent gas, a volumetric reagent gas flow rate of 0.0003 to 0.3 atmosphere ml/min is required. The reagent gas is typically supplied from a pressurized bottle, with the source pressure being substantially above atmospheric pressure. A high source pressure is required for the pressure regulator to properly function and provide a stable pressure from a restricting mechanism. The large pressure differential which is placed across the gas flow control mechanism, coupled with the requirement of extremely small reagent gas flow rates has lead to the use, in prior art systems, of expensive and complicated mechanical variable restrictor valves. These valves, often called "micro leak valves", must be fabricated from high precision mechanical components. The components that are used in commercially available valves have high temperature coefficients, so that such valves are highly temperature sensitive.

In prior art reagent gas flow control systems for ion trap mass spectrometers, a solenoid valve is used in series with and downstream from the micro leak valve to turn the gas flow on and off. For example, the reagent gas might be turned off while the user of the ion trap conducts EI mass spectrometry. Later the valve may be turned on to allow the user to conduct a CI experiment. When the solenoid valve is in the off position, i.e., the reagent gas flow is turned off, pressure builds up behind the valve. Thereafter, when the solenoid valve is switched "on" to allow the reagent gas to flow, there will be a significant pressure "surge" into the ion trap due to the build up of pressure behind the solenoid valve. This large pressure surge requires that the electronics of the ion trap be turned off before, and for some time after the valve is turned on. Otherwise, the rf electronics, the electron multiplier, and the electron emission filament are subject to potential damage. This disruption causes drift and instability for a period of time.

Accordingly, it is the object of the present invention to provide a reagent gas flow control system which is less expensive and more reliable than those of the prior art.

Another object of the present invention is to provide a gas flow control system for delivering reagent gas to an ion trap mass spectrometer which can be turned off and on without causing pressure surges within the ion trap.

Yet another object of the present invention is to provide a gas flow control system which delivers a controlled low volume of gas at low pressure using simple, readily available component parts.

Still another object of the present invention is to provide a gas flow control system which is less temperature dependent, yet just as accurate as those of the prior art.

SUMMARY OF THE INVENTION

The foregoing objects of the present invention, and others that will be apparent to those skilled in the art, are realized in the new gas flow control system described herein. The system consists of a source of a desired gas which is to be introduced into a vacuum chamber where it is to be used. The gas source is linked to the vacuum chamber by a conduit containing a switching means for turning the gas flow on and off. At least two gas restrictors are also positioned along the conduit, and a pressure re means is connected to the conduit between the two gas flow restrictors. In a preferred embodiment the pressure reducing means comprises a second conduit connecting the first conduit, at a point between the two restrictors, to the vacuum pump for the overall system. A third gas flow restrictor may be positioned in the second conduit, and at least one of the restrictors may be a variable restrictor.

BRIEF DESCRIPTION OF THE DRAWINGS

FIG. 1 is a schematic diagram of a gas flow control system of the type known in the prior art, used in connection with an ion trap mass spectrometer.

FIG. 2 is a schematic diagram of one embodiment of a gas flow control system of the present invention.

FIG. 3 is a schematic diagram of a second embodiment of a gas flow control system of the present invention.

FIG. 4 is a schematic diagram of a third embodiment of a gas flow control system of the present invention.

FIGS. 5A and 5B are chromatogram plots of the output of a ion trap mass spectrometer employing the gas flow control system of the present invention at masses 69 and 414, respectively.

FIGS. 5C and 5D are detailed portions of the chromatogram plots of FIGS. 5A and 5B, respectively, centered around scan number 60.

DETAILED DESCRIPTION

FIG. 1 schematically shows a prior art gas flow control system for introducing a reagent gas into an ion trap mass spectrometer for performing mass analysis in the chemical ionization mode. A source of a suitable reagent gas 5, typically contained in a pressurized bottle, is connected to the ion trap 10, by way of gas conduit 15. Ion Trap 10 is held at a greatly reduced pressure by a vacuum pumping system, which may consist of a roughing pump 20 and a turbomolecular pump 25, as is well known in the art. Typically, the operating pressure within the ion trap is about $2 \times 10^{-3}$ Torr helium. Sample is introduced into the ion trap from a source of sample gas, which may consist of a standard gas chromatograph 30. A gas chromatograph is useful for this purpose because it separates complex samples into their components, thereby making the mass analysis much easier to perform.

Along the flow path of conduit 15, positioned between the reagent gas source 5 and the ion trap 10, are a variable restrictor 40, also referred to as a metering or micro leak valve, and a solenoid actuated gate valve 50. As explained above, in order to provide reagent gas at a suitably low flow rate to achieve the proper reagent gas pressure level in the ion trap, restrictor 40 comprises a high precision micro leak valve. The gas control metering valve must be of the type which functions over a very large pressure drop. Not only are such valves relatively expensive but, due to the components from which they are fabricated, micro leak valves are quite temperature sensitive. Accordingly, it is necessary to operate system so that restrictor 40 is held at a relatively constant temperature.

Gate valve 50 is required so that the flow of reagent gas can be shut off. For example, it is necessary to shut off the flow of reagent gas when the ion trap is being used to conduct experiments in the electron impact ionization mode. It will be apparent to those skilled in the art that when gate valve 50 is closed, pressure will build up behind the valve until both sides of restrictor 40 reach equilibrium. Thereafter, when gate valve 50 is opened, there will be a pressure surge of reagent gas into the ion trap. As explained above, this requires that some of the system electronics be turned off to avoid damage until the pressure within the ion trap is again reduced to its operating level. Gate valve 50 must be located downstream of restrictor 40 in order to achieve adequate on/off control of the reagent gas flow. If gate valve 50 were to be positioned upstream of restrictor 40, then the flow of gas into the ion trap would continue for an appreciable time after shutting of the gate valve until pressure equilibrium across the micro leak valve were reached.

Turning now to FIG. 2, a preferred embodiment of the present invention is shown in schematic form. Those components of the system which are the same as the components shown in FIG. I are given the same numbers. The system of FIG. 2 includes a source of reagent gas 5 which is connected to the ion trap 10 by conduit 15 having two portions 15a and 15b. Also connected to the ion trap are a gas chromatograph 30 and a vacuum pumping system comprising roughing pump 20 and turbomolecular pump 25. In one embodiment, roughing pump 20 is an Alcatel pump with a two cubic feet per minute pumping capacity. The turbomolecular pump is a Varian model V-60, with a pumping speed of 60 liters/sec. Those skilled in the art will recognize that other types of vacuum pumps may be substituted.

Between conduit portions 15a and 15b is a tee connector 60 which connects a second conduit 65 between the tee connector and the roughing pump 20. In the embodiment of FIG. 2, a solenoid actuated gate valve 50 is used to turn the flow of reagent gas into the ion trap on and off. Within first conduit portion 15a, i.e., between the reagent gas source 5 and the tee connector 60, is a first fixed gas flow restrictor 80. Likewise, within second conduit portion 15b, i.e., between the gate valve 50 and the tee connector 60, is a second fixed gas flow restrictor 70. First and second fixed restrictors 70 and 80 may be simply and inexpensively constructed; for example, from lengths of stainless steel capillary tubing. Stainless steel tubing having an inner diameter of 5 mils, an outer diameter of 60 mils and a length in the range of 10 to 25 inches has been found to be suitable for this purpose.

A variable restrictor 90 is positioned along conduit 65, between tee connector 60 and roughing pump 20. Variable restrictor 90 may be a simple needle valve; for example, a needle valve of the type commercially available from Porter Precision Valve, model number HR 3. In operation, by selecting a first fixed restrictor of a proper value and adjusting the variable restrictor valve, it is possible to establish a predetermined vacuum level at tee connector 60. For example, variable restrictor 90 may be adjusted to provide a vacuum level of 100-0.1 Torr at tee connector 60. Accordingly, the pressure differential across fixed restrictor 80 is greatly reduced. Likewise, since a major portion of the pressure in the system in dropped across first fixed restrictor 70, the pressure drop across variable restrictor 90 is greatly reduced and, thus, restrictor 90 need not have the precision of those used in the prior art.

When gate valve 50 is off, the pressure at the upstream end of second fixed restrictor 80, i.e., at tee connector 60, remains relatively low, so that when the gate valve is opened the pressure surge is negligible. This is due to the fact that shutting gate valve 50 does not stop the flow of gas through restrictors 70 and 90 to vacuum pump 20. This allows actuation of gate valve 50 without concern for whether the system electronics are on or off.

A second embodiment of the flow control system of the present invention is shown schematically in FIG. 3, wherein similar parts are, again, given the same numbers. The design of this embodiment is similar to that of the FIG. 2 embodiment, except that a fixed restrictor 95 is used between tee connector 60 and vacuum pump 20 and a variable restrictor 110 is used between the tee connector and ion trap 10. Again, by selecting properly sized fixed restrictors 70 and 95, it is possible to obtain a generally predetermined vacuum level at tee connector 60. In the design of FIG. 3, rather than use a separate variable restrictor and gate valve, an integrated linear valve 100 may be utilized. Such a valve, which may be purchased from General Valve, model no. 9-556, may be electronically controlled to be fully open, fully closed, or at some intermediate position which provides a desired level of flow restriction. Valve 100 is equivalent to the variable flow restrictor and a gate valve shown within the dashed lines of FIG. 3 and numbered 110 and 120 respectively. Again, since the pressure level at tee connector 60 is well below atmospheric pressure, opening and closing linear valve 100 does not cause any appreciable pressure surge into the ion trap.

Another embodiment of the present invention is shown in FIG. 4, wherein similar parts are, again, given the same numbers. In this embodiment, a first fixed restrictor 95 is positioned between tee connector 60 and vacuum pump 20 and a second fixed restrictor 80 is positioned between tee connector 60 and ion trap 10. A linear valve 130, similar to that described above in reference to FIG. 3, is positioned between reagent gas source 5 and tee connector 60. Again, linear valve 130 may be depicted as a combination of a variable restrictor 140 and a gate valve 150. It should be noted that in the designs of FIGS. 2 and 3, the flow of reagent gas is continuous through the system to the vacuum pump 20, even when gate valves 50 or 120 is closed. This assures that the pressure level at tee connector 60 remains constant. However, these configurations result in wasted gas. Moreover, in all of the embodiments that have been described, a significant portion of the reagent gas flows to the vacuum pump without ever entering the ion trap. Nonetheless, the reagent gases used in CI are normally relatively inexpensive so that the advantages of the present system outweigh any added expense associated with wasted reagent gas. The FIG. 4 embodiment mitigates the loss of reagent gas by placing a gate valve 150 between the gas source 5 and vacuum pump 20. This embodiment is less preferred, however, because the pump out time for gas in the portion of the conduit 15a downstream of the solenoid and in conduit 15b is limited by the conductance through restrictors 80 and 95. Thus, in this arrangement there is a delay between the time that the gate valve or solenoid is shut and the stoppage of reagent gas flow into the ion trap.

In each of the embodiments of the present invention that have been described, the variable restrictor operates at flow rates that are orders of magnitude higher that those used in the prior art, and thus are simpler and lower in cost than the prior art devices. Moreover, much of the flow restriction is provided by fixed restrictors that inherently have lower temperature coefficients than variable restrictors. It can be shown, for example, that in the embodiment of FIG. 2, the flow into the ion trap depends on the ratio of fixed restrictor 80 ($R_3$) to variable restrictor 90 ($R_2$). Since fixed restrictors have inherently lower temperature coefficients than variable restrictors, the effect of the temperature coefficient of variable restrictor 90 is reduced in proportion to the ratio of restrictor 80 to restrictor 90 ($R_3/R_2$).

In comparisons between the prior art design and the design of the present invention, the absolute responses of the prior art device were found to vary between 15 and 20 percent, while those of the present invention were found to vary between 1 and 5 percent.

FIGS. 5A and B are chromatograms, for masses 69 and 414, respectively, which show the effect of turning the flow of reagent gas into the ion trap on and off. It can be seen that no pressure surge is observable when the gate valve is turned on, so that the electronics can be left on during the process without any detrimental effects. FIGS. 5C and D ar enlargements of a portion of the chromatograms of FIGS. 5A and B, showing specifically the response between scans 60 and 61. The scan rate was set at one per second, and thus the opening of the valve and the stabilization occurs in less than one second. Scan 60 was performed with the reagent gas off and scan 61 was performed with the reagent gas on. Mass 414 was monitored in the sample of perfluortributyl amine, since it has a small response in the absence of reagent gas and a large response when subject to chemical ionization.

While the present invention has been described in connection with several preferred embodiments thereof, those skilled in the art will recognize that other changes and embodiments may be made without departing from the spirit thereof. Accordingly, the scope of the present invention should be construed only with reference to following claims.

I claim:

1. An apparatus for introducing a precisely controlled flow of a desired gas into a vacuum chamber, comprising:
   a source of the desired gas,
   a vacuum chamber,
   a first fluid conduit linking the gas source with the vacuum chamber,
   switching means along said conduit for turning the flow of gas to said vacuum chamber on and off,
   at least two gas flow restriction means along said first conduit for controlling the flow of gas into the vacuum chamber when said switch is one, and
   pressure reducing means comprising vacuum pumping means, connected to said first conduit between said at least two gas flow restriction means, for preventing the accumulation of pressure between said at least two gas flow restriction means when said switch is off, said vacuum pumping means also being connected to said vacuum chamber.

2. The gas flow control apparatus of claim 1 wherein each of said gas flow restriction means is a fixed gas flow restrictor.

3. The gas flow control apparatus of claim 2 wherein said fixed gas flow restrictors comprises a length of capillary tubing.

4. The gas flow control apparatus of claim 1 wherein one of said gas flow restriction means is a variable gas flow restrictor.

5. The gas flow control apparatus of claim 1 wherein said pressure reducing means further comprises a second conduit connected at one end to said first conduit and at its other end to said vacuum pumping means.

6. The gas flow control apparatus of claim 5 further comprising additional gas flow restriction means within said second conduit.

7. The gas flow control apparatus of claim 6 wherein said additional gas flow restriction means is a fixed gas flow restrictor.

8. The gas flow control apparatus of claim 7 wherein said additional fixed gas flow restrictor comprises a length of capillary tubing.

9. The gas flow control apparatus of claim 6 wherein said additional gas flow restriction means is a variable gas flow restrictor.

10. A gas control system for introducing a flow of gas at low-pressure into a vacuum chamber, comprising:
first gas flow restriction means having an input end and an output end, said input end being connected to a source of gas which is to be introduced into said vacuum chamber at low pressure,
second gas flow restriction means having an input end and an output end, said input end being connected to the output end of said first gas flow restriction means, and the output end of said second gas flow restriction means being connected to the vacuum chamber,
vacuum pumping means for evacuating the interior of the vacuum chamber,
third gas flow restriction means having an input end and an output end, and connected at its input end with the output end of said first gas flow restriction means and with the input end of said second gas flow restriction means, the output end of said third gas flow restriction means being connected to said vacuum pumping means,
gas flow switching means in the fluid path between said source of gas and said vacuum chamber,
wherein at least one of said gas flow restriction means is adjustable.

11. The gas control system of claim 10 wherein said gas flow switching means comprises a gate valve.

12. The gas control system of claim 10 wherein said source of gas is at a pressure which exceeds atmospheric pressure and the gas flow restriction means are set to provide a pressure at the input end of said third gas flow restriction means which is substantially below atmospheric pressure.

13. The gas flow restrictor of claim 10 wherein said first gas flow restriction means is greater than said second gas flow restriction means, such that most of the pressure drop between the source of gas and said vacuum chamber is across said first gas flow restrictor.

14. An ion trap mass spectrometer having a gas flow control system for introducing a reagent gas at low pressure into a the ion trap for conducting chemical ionization mass spectroscopy at low pressure, comprising:
an ion trap;
a source of pressurized reagent gas;
vacuum pumping means for maintaining a desired vacuum within said ion trap;
a first gas flow restrictor connected at one end to said reagent gas source, and at the other end to a tee connector;
a second gas flow restrictor connected at one end to said tee connector, and at the other end to said ion trap;
a third gas flow restrictor connected at one end to said tee connector and at the other end to said vacuum pumping means;
whereby the pressure at said tee connector is substantially less than atmospheric pressure.

15. The system of claim 14 further comprising gas into the ion trap on and off.

16. The system of claim 14 wherein at least one of said gas flow restrictors is a variable restrictor.

17. The system of claim 14 wherein said vacuum pumping means comprises a roughing pump and said third gas flow restrictor is connected to said roughing pump.

18. The system of claim 14 further comprising a gas chromatograph for introducing a sample to be analyzed into the ion trap.

19. A method of introducing a reagent gas into an ion trap mass spectrometer for conducting chemical ionization experiments comprising the steps of:
providing a pressurized source of reagent gas;
flowing said reagent gas through a first gas flow restrictor;
splitting the flow of reagent gas exiting said first gas flow restrictor into two parts;
flowing the first part of said split gas flow through a second gas flow restrictor and, thereafter, into said ion trap;
flowing the second part of said split gas flow through a third gas flow restrictor and, thereafter, to a vacuum pump.

20. The method of claim 18 further comprising the step of adjusting one of said gas flow restrictors so that reagent gas flows into said ion trap at a desired rate.

21. An apparatus for introducing a precisely controlled flow of a desired gas into a detection chamber of an analytical instrument, said detection chamber being of the type which is operated at subatomospheric pressure, comprising:
a source of the desired gas,
a detection chamber,
a first fluid conduit linking the gas source with the detection chamber,
switching means along said conduit for turning the flow of gas to said detection chamber on and off,
at least two gas flow restriction means along said first conduit for controlling the flow of gas into the detection chamber when said switch is on, and
pressure reducing means, connected to said first conduit between said at least two gas flow restriction means, said pressure reducing means comprising a second conduit connected at one end of said first conduit and at its other end to vacuum pumping means, said vacuum pumping means being also being connected to said detection chamber, such that the accumulation of pressure between said at least two gas flow restriction means when said switch is off is substantially prevented.

22. A gas control system for introducing a flow of gas at low-pressure into a detection chamber of an analytical instrument, said detection chamber being of the type which is operated at subatmospheric pressure, comprising:

first gas flow restriction means having an input end and an output end, said input end being connected to a source of gas which is to be introduced into said detection chamber at low pressure, second gas flow restriction emans having an input end and an output end, said input end being connected to the output end of said first gas flow restriction means, and the output end of said second gas flow restriction means being connected to the detection chamber, vacuum pumping means for evacuating the interior of the detection chamber, third gas flow restriction means having an input end and an output end, and connected at its input end with the output end of said first gas flow restriction means and with the input end of said second gas flow restriction means, the output end of said third gas flow restriction means being connected to said vacuum pumping means, gas flow switching means comprising a gate valve in the fluid path between said source of gas and said detection chamber, wherein at least one of said gas flow restriction means is adjustable and wherein said adjustable gas flow restriction means and said gate valve are combined into an integral unit.

* * * * *